United States Patent [19]
Llanos

[11] Patent Number: 5,507,804
[45] Date of Patent: Apr. 16, 1996

[54] CROSS-LINKED POLYETHYLENE OXIDE COATINGS TO IMPROVE THE BIOCOMPATIBILITY OF IMPLANTABLE MEDICAL DEVICES

[75] Inventor: Gerard Llanos, Fort Worth, Tex.

[73] Assignee: Alcon Laboratories, Inc., Fort Worth, Tex.

[21] Appl. No.: 340,671

[22] Filed: Nov. 16, 1994

[51] Int. Cl.$^6$ .................... A61F 2/02; A61F 2/16
[52] U.S. Cl. ................ 623/11; 623/6; 427/2.1; 427/2.27
[58] Field of Search .................. 623/4, 6, 8, 11, 623/15; 427/2.1, 2.27; 523/113, 115

[56] References Cited

U.S. PATENT DOCUMENTS

| | | | |
|---|---|---|---|
| 4,170,043 | 10/1979 | Knight et al. | 3/13 |
| 4,280,970 | 7/1981 | Kesting | 264/1.7 |
| 4,312,575 | 1/1982 | Peyman et al. | 351/160 |
| 4,656,083 | 4/1987 | Hoffman et al. | 428/265 |
| 4,834,750 | 5/1989 | Gupta | 623/6 |
| 4,871,785 | 10/1989 | Froix | 523/106 |
| 4,961,954 | 10/1990 | Goldberg et al. | 427/2 |
| 4,973,493 | 11/1990 | Guire | 427/2 |
| 5,002,794 | 3/1991 | Ratner et al. | 427/41 |
| 5,070,166 | 12/1991 | Su et al. | 526/301 |
| 5,080,924 | 1/1992 | Kamel et al. | 427/2 |
| 5,094,876 | 3/1992 | Goldberg et al. | 427/2 |
| 5,100,689 | 3/1992 | Goldberg et al. | 427/2 |
| 5,116,361 | 5/1992 | Kim et al. | 623/1 |
| 5,169,720 | 12/1992 | Braatz et al. | 428/423.1 |
| 5,252,714 | 10/1993 | Harris et al. | 530/391.9 |
| 5,275,838 | 1/1994 | Merrill | 427/2 |
| 5,290,548 | 3/1994 | Goldberg et al. | 424/78.18 |
| 5,290,892 | 3/1994 | Namdaran et al. | 526/259 |
| 5,308,641 | 5/1994 | Cahalan et al. | 427/2 |
| 5,326,584 | 7/1994 | Kamel et al. | 427/491 |
| 5,331,073 | 7/1994 | Weinschenk, III et al. | 526/264 |

OTHER PUBLICATIONS

Sheu et al., "Immobilization of polyethylene oxide surfactants for non–fouling biomaterial surfaces using an argon glow discharge treatment," *J. Adhesion Sci. Technol.*, vol. 7, No. 10, pp. 1065–1076 (1993).

Product Brochure from Advanced Surface Technology, Inc., "Biophilic™ Coating" (no date).

*Primary Examiner*—Paul B. Prebilic
*Attorney, Agent, or Firm*—Patrick M. Ryan

[57] ABSTRACT

Polyethylene oxide (PEO) coatings providing improved biocompatibility for implantable medical devices are disclosed. The PEO coatings comprise functionalized end-capped PEO which is attached at one end to the medical device. The PEO compounds are then exposed to a high energy source for a time sufficient to cause the PEO compounds to form a cross-linked, insoluble network. These PEO coatings are able to survive ethylene oxide sterilization procedures with minimal loss of protein or cell repulsion ability.

6 Claims, No Drawings

CROSS-LINKED POLYETHYLENE OXIDE COATINGS TO IMPROVE THE BIOCOMPATIBILITY OF IMPLANTABLE MEDICAL DEVICES

FIELD OF THE INVENTION

This invention relates to implantable medical devices. More particularly, this invention relates to cross-linked polyethylene oxide coating materials and methods which preserve the biocompatibility of implantable medical devices that are sterilized by ethylene oxide sterilization procedures. The polyethylene oxide coating materials are cross-linked by exposure to a high energy source.

BACKGROUND OF THE INVENTION

The biocompatibility of implantable medical devices can be improved by a variety of known methods, most notably by surface modification, such as the addition of a coating material. For example, it is known that ophthalmic lenses may be coated with a coating material. U.S. Pat. No. 4,170,043 discloses intraocular lenses (IOLs) coated with a film that dissolves slowly in water. This helps prevent endothelial damage upon implantation of the IOL. The coating dissolves within about 24 hours after implantation.

U.S. Pat. No. 4,731,080 discloses a coated IOL, wherein the lens is coated with a non-smudging, biologically compatible hydrophobic cross-linked vinyl-containing silicone polymer coating material.

U.S. Pat. No. 5,080,924 discloses a method of modifying the surface of a substrate using radio frequency plasma-induced grafting. In this procedure, which may be used on an IOL, a first biocompatible material, preferably having pendant carboxylic acid or amine groups, is covalently grafted to the surface of a substrate polymer core by radio frequency plasma induction. A second biocompatible material then may be grafted to the first biocompatible material using a cross-linking agent.

A series of patents disclose contact lenses which are coated by various materials including polyethylene oxide (PEO). Such patents include U.S. Pat. Nos. 4,280,970; 4,871,785; 4,740,533; 5,070,166; and 5,096,626. U.S. Pat. No. 4,280,970 discloses coating a contact lens by grafting PEO thereto.

U.S. Pat. No. 5,308,641 discloses an improved spacer material for improving the biocompatibility of a biomaterial and a method for making it, in which a polyalkylimine is covalently attached to an aminated substrate and combined with a cross-linking agent which is at least difunctional in aldehyde groups. The polyalkylimine can be, for example, polyethyleneimine and the cross-linking agent can be, for example, glutaraldehyde. Preferably, the cross-linking agent is applied in dilute solution and at a pH suitable to accomplish light cross-linking of the polyalkylimine and also provide aldehyde linkages at the interface between the biomolecule and the spacer.

U.S. Pat. No. 5,290,548, assigned to the University of Florida, discloses PEO coated instruments, devices, implants, contact lenses and the like. The PEO coating is created using gamma radiation to polymerize vinyl-functionalized PEO directly onto the surface of the instrument, device, etc.

U.S. Pat. No. 4,973,493 discloses a method for modifying a surface to improve its biocompatibility. The method employs molecules of a biocompatible agent and a chemical linking moiety possessing two different photochemically reactive groups, one group which reacts with the surface and one which reacts with the biocompatible agent. The method comprises applying stimulus to sequentially activate the groups to covalently bind the linking moiety to the molecules of the biocompatible agent and to photochemically covalently bind the linking moiety to the surface of the device. In one embodiment, the molecules of the biocompatible material are joined together to form a film that is attached to the surface of the device by the linking moiety. In this embodiment, the biocompatible agent desirably may be hyaluronic acid or albumin. A biocompatible device having such a film attached may be an artificial hip joint coated with a film of hyaluronic acid. No mention is made of sterilization of the devices.

Commonly assigned, co-pending U.S. patent application Ser. No. 08/166,033, discloses intraocular lenses coated with PEO applied through amine covalent bonding. However, when these lenses are sterilized with ethylene-oxide (EtO) sterilization and then aerated to remove residual EtO, some of the protein and cell repulsion ability of the PEO coating is lost. U.S. Ser. No. 08/166,033 discloses an aqueous extraction step in place of the conventional aeration step to minimize the coating's loss of protein and cell repulsion ability.

What is needed are additional coatings and processes for improving the biocompatibility of implantable medical devices which must survive EtO sterilization procedures.

SUMMARY OF THE INVENTION

The present invention provides PEO coatings and methods for improving the biocompatibility of implantable medical devices. The PEO coatings of the present invention comprise PEO which is capped with functionalized groups on at least one end, wherein the PEO coatings are formed by attaching the functionalized end of the PEO compounds to the implantable medical device, and then cross-linking the PEO compounds by exposing them to a high energy source prior to ethylene oxide sterilization.

Among other factors, the present invention is based on the finding that exposing PEO coating compounds which have been attached to an implantable medical device to a high energy source for a time sufficient to cause the PEO molecules to form a cross-linked, insoluble network minimizes the coating's loss of protein and/or cell repulsion ability when the coating is subjected to EtO sterilization procedures.

DETAILED DESCRIPTION OF THE INVENTION

As used herein, implantable medical device means any article, derived from synthetic or semi-synthetic material, that when placed in the appropriate biological location serves to replace or enhance or monitor the performance of a target tissue/organ. These include but are not limited to substitute blood vessels, catheters, intraocular lenses, contact lenses, electrodes, hydrocephalus and abdominal shunts, etc.

As used herein, "biocompatible" or "biocompatibility" means being compatible with biological tissue/fluids either in a living organism or a system consisting of a mixture of biological components (protein and/or cell based), not eliciting any changes in the structure or function of any of the biological components that will ultimately compromise or negatively affect the biological system or organism.

As used herein, "high energy source" means a source which results in the formation of free radicals, ions, electrons, protons, neutrons, alpha particles, beta particles, gamma radiation, X-ray radiation and/or ultraviolet radiation. These energy sources include but are not limited to radio-frequency glow discharge plasma (rf-plasma), electron beam, gamma, and ultraviolet sources.

The coatings of the present invention may be applied to the surface of any implantable medical device on which it may be desirable to minimize protein adsorption and cellular deposition. For purposes of illustration, examples relating to IOLs will be presented; however, one skilled in the art will readily appreciate that the coatings of the present invention may be applied to any implantable medical device.

In the case where the implantable medical device is an IOL, the improved coatings of the present invention may be applied to any of the well known hard IOLs, such as those formed from polymethylmethacrylate (PMMA). The improved coatings of the present invention may also be applied to soft acrylic lenses, such as those disclosed in U.S. Pat. Nos. 4,834,750; 5,290,892; and 5,331,073; the entire contents of each of these three references are hereby incorporated into this disclosure. Additionally, as one skilled in the art would readily appreciate, the improved coatings of the present invention may be applied to other types of lens materials, for example silicone materials. In a preferred embodiment, improved coatings of the present invention are applied to lenses formed from a copolymer with an elongation of at least 150% wherein the copolymer is formed from two monomers, the first of which is 2-phenylethyl acrylate and the second of which is 2-phenylethyl methacrylate, and a copolymerizable cross-linking monomer having a plurality of polymerizable ethylenically unsaturated groups such as 1,4-butanediol diacrylate. The first monomer may be present at a concentration about 65 wt. % and the second monomer may be present at a concentration of about 30 wt. %. An ultraviolet absorbing material such as 2-(3'-methallyl'-2-hydroxy-5'-methyl-phenyl) benzotriazole may also be included.

According to the present invention, the biocompatibility of IOLs or other implantable medical devices is substantially improved by coating them with a PEO coating which is cross-linked prior to sterilization. In particular, the PEO-coated lenses or other devices have improved resistance to protein adsorption. This results in a lens or other device which is "non-fouling" and resistant to cell deposition.

The PEO coatings of the present invention are first tethered to the substrate surface. There are a number of known methods for attaching PEO chains to substrate surfaces. One skilled in the art will readily recognize that these known methods include, for example, wet chemical methods, such as those providing electrostatic interactions or covalent bonding, and dry methods such as high energy plasma deposition.

In a preferred embodiment, the PEO coating is attached to the IOL or substrate surface through covalent bonding. The substrate surface is first provided with an active coating or layer. Preferably, the active layer is a polymer coating containing a primary amine. However, other active layers which function to tie PEO compounds to substrate surfaces may also be used.

The primary amine layer is preferably formed by contacting the substrate surface with an allyl amine or a lower alkyl amine of the formula $RNH_2$, wherein R is an alkyl or allyl group of about 3–12 carbon atoms. Preferably the alkyl or allyl amine is one of intermediate chain-length wherein R is an alkyl group of 5–8 carbons. Most preferably, the alkyl or allyl amine is n-heptyl amine.

The alkyl or allyl amine may be applied to the substrate surface in any desired manner; however, it is preferred to create the active primary amine layer by plasma deposition of the alkyl or allyl amine. Plasma deposition in general is known in the art as shown for example in U.S. Pat. Nos. 4,312,575 and 4,656,083, the disclosures of which are incorporated by reference.

Plasma deposition of the primary amine layer on the substrate surface is preferably carried out in two steps. In the case of an IOL, the lens is first placed in an electrical glow discharge apparatus, preferably oriented with the optical surfaces parallel to direction of gas flow. A gaseous atmosphere is provided, (e.g., argon), and then the gaseous atmosphere is subjected to an electrical glow discharge to clean the surface. The gas is then removed. In the second step, plasma ignition is carried out in the presence of the vapor of the primary amine under conditions to cause the amine to deposit or form a plasma and produce an ultrathin coating of about 5–300 Angstroms on the surface of the lens.

After treatment with the amine, the substrate surface containing the amine layer is then reacted with functionalized end-capped PEO in the presence of a reducing agent to give a stable PEO coating covalently bound to the substrate surface. The PEO should have terminal groups or caps which are reactive with the amine coating. While it is not necessary that both ends of the PEO chains have reactive terminal groups, a preferred PEO utilized in the present invention is an $\alpha,\omega$-aldehyde-terminated PEO having a molecular weight in the range of 200 to 100,000, preferably 1500–15,000. Most preferred is an $\alpha,\omega$-aldehyde-capped PEO having a molecular weight of about 8000. Mono- and di-aldehyde-capped polyethylene oxides are known in the art, e.g., Harris, U.S. Pat. No. 5,252,714.

The alkyl or allyl amine is applied by plasma deposition as indicated above. In a preferred procedure, the IOL or substrate surface is first etched prior to amine deposition for best results. Preferably, etching of the surface is conducted by contact with an argon plasma. An argon flow rate in the range of 60–120 $cm^3$/min, and a chamber pressure of 200–300 mTorr is satisfactory in conducting the deposition, the IOL or other implantable medical device is placed in a holder and centered in a plasma chamber with the desired argon-plasma flow rate to argon etch prior to amine deposition. A container for the amine is connected to the plasma chamber unit. The plasma chamber is then evacuated to its baseline pressure and, while under the argon flow rate, is ignited for a short period, for example, 60W for six minutes. After the argon-plasma etch, the plasma chamber is evacuated to its baseline pressure, the amine vapor is evacuated into the chamber, the plasma ignited, and the deposition permitted to be maintained until a thickness in the range of 5–500, preferably 100–300 Angstroms, is achieved. After the plasma is extinguished, the chamber conditions are maintained for a short period, for example, 1–5 minutes. The chamber is then brought to atmospheric conditions and the sample removed to a sealed container.

PEO, e.g., $\alpha,\omega$-aldehyde-capped polyethylene oxide, is dissolved in a buffer solution in a concentration in the range of 5–50 mg/ml. This solution is then added to each container with the amine-plasma coated IOL or other device. Stabilization of the coating is then carried out, for example, by treating the IOL or other device with a stabilizing agent, such as an alkali metal borohydride, dissolved in a buffer in a concentration of 10–50 mg/ml. The reaction is then carried out at a low temperature, for example, 25°–50° C. for about ten to thirty hours. Low temperatures are used in order to avoid thermal degradation of the PEO compounds.

The preferred stabilizing agent is sodium cyanoborohydride of the formula $NaCNBH_3$, a commercially available material. Reduction of the PEO-imine bond with the alkali metal borohydride will provide a stable PEO coating of about 5–500 Angstroms, preferably 100–300 Angstroms. In a preferred procedure, stabilization is repeated and the IOLs or other implantable medical devices are again heated. Each IOL or other device is then washed in deionized water and the water removed.

The procedure described above is only one method of tethering functionalized end-capped PEO chains to substrate surfaces. Any alternative procedure which tethers a functionalized end-capped PEO chain to substrate surfaces may also be used.

An important aspect of the invention concerns sterilization of the IOLs or other devices after preparation. As used herein, "EtO sterilization" comprises contacting the IOL or other device with 5–100% ethylene oxide in a fluorinated solvent for 1–4 hours at 10–40 psi and 40°–60° C., preferably after preconditioning in a humid atmosphere, followed by aeration to remove residual ethylene oxide. IOLs or other implantable medical devices coated in the above manner which are sterilized using EtO sterilization lose some of their protein and cell repulsion ability.

According to this invention, it has been discovered that exposing PEO coatings which have been tethered to a substrate surface to a high energy source for a time sufficient to cause the PEO molecules to form a cross-linked, insoluble network minimizes the coating's loss of protein and/or cell repulsion ability when subjected to EtO sterilization procedures. Such high energy irradiation can be achieved by exposing the coated IOL to an inert gas if-plasma. However, as one skilled in the art would readily appreciate, exposing the PEO coating to other high energy sources, such as those which generate accelerated electrons, protons, neutrons, alpha particles, beta particles, gamma radiation, X-ray radiation, and/or ultraviolet radiation would also cause the PEO molecules to form a cross-linked, insoluble network.

In a preferred embodiment, the PEO coating is exposed to an argon plasma for 20–90 seconds. With a chamber pressure of 200–300 mTorr, an argon flow rate of 60–120 $cm^3/min$ is ignited at 40–80 watts to obtain a plasma. One skilled in the art would realize that the pressure levels, power levels and exposure times are influenced by such variables as reactor configuration, substrate material and gas.

Without wishing to be bound by theory, it is hypothesized that the PEO chains must be able to achieve a fully extended conformation, through solvent-polymer interaction, and to be able to have free rotation about the single bonds of its backbone, i.e., for the chains to have a "flagella-like" motion, creating a dynamic barrier on the surface of the substrate to which it is immobilized so as to provide maximum resistance against protein adsorption or cell deposition. Driven by interfacial forces, native PEO strands, immobilized through one terminal, may become wholly or partially buried beneath the substrate surface during EtO sterilization procedures, thereby losing their ability to resist fouling. Though cross-linking may reduce the flagella-like motion of the PEO strands, it may serve to prevent burial of the PEO strands beneath the substrate surface.

The following examples are presented to illustrate the invention but are not intended to limit it in any way.

EXAMPLE 1

A. Surface Animation:

IOLs made of PMMA held in position by a polyethylene lens holder placed in small glass-rack, are centered in a plasma chamber on a glass rack. The rack is positioned with the optic surface oriented parallel to the monomer flow. Any plasma chamber capable of holding the device to be coated can be used. In this case, the plasma chamber was made of a glass cylinder approximately 25 cm in diameter and 55 cm long, wrapped in four quadrants with four copper electrodes (two hot and two ground) each 49 cm×17 cm.

n-Heptylamine (5 g) is placed in a 250 ml round-bottom flask which is connected to the plasma chamber via a metering-valve. With this valve closed, the plasma chamber is evacuated to its baseline pressure for 30 minutes. Prior to heptylamine deposition, the IOLs are argon-plasma etched. With an argon flow rate of 90 $cm^3/min$ and a chamber pressure of 250 mTorr, the chamber is equilibrated for ten minutes. A plasma is then ignited at 60 W for 6 minutes. After the argon-plasma is extinguished, the chamber is returned to its baseline pressure.

With the plasma chamber's vacuum pump speed on a low setting (baffle position to approximately 5°; 90° represents maximum pump rate) heptylamine vapor is evacuated into the chamber. The chamber is allowed to equilibrate for ten minutes. At a rf power of 60 watts a plasma is ignited, and the thickness gauge activated to record deposition. The plasma is maintained until a thickness of approximately 200 Å is achieved. After the plasma is extinguished the chamber conditions are maintained for 2 minutes. Following this the vacuum pump speed is returned to maximum and these conditions are maintained for ten minutes. The chamber is then brought up to atmospheric conditions by back-filling with argon and the samples removed from their respective holders. Each is placed in a labelled micro-centrifuge tube.

B. PEO Immobilization:

Dithiolaldehyde-derivatized PEO, which can be synthesized following methods described by Harris et al., U.S. Pat. No. 5,252,714, is dissolved in a 0.0042M sodium phosphate (dibasic)—0.45M potassium sulphate buffer (pH 8.5–9.0) at a concentration of 10 mg/mL. 900 μL of this solution is added to each micro-centrifuge tube containing plasma-coated IOL. Sodium cyanoborohydride ($NaCNBH_3$) is dissolved in buffer at a concentration of 20 mg/mL. 100 μL of this solution is added to each micro-centrifuge tube, and after gentle mixing the samples are heated at 35° C. overnight. Note that the $NaCNBH_3$ solution is prepared just prior to its addition to the reaction solution. A second treatment with $NaCNBH_3$ solution is then applied and samples heated at 35° C. for another four hours. The samples are then removed from the reaction solution, washed extensively in deionized water, and air dried.

C. Cross-Linking:

Each sample is mounted in a lens holder and placed in a glass rack. This rack is centered in the plasma chamber used in Step A and the system evacuated to baseline pressure for ten minutes. The chamber is equilibrated for five minutes with argon at 250 mtorr and a flow rate of 90 $cm^3/min$. A plasma is ignited at 60 watts for 20 seconds. After the plasma is extinguished, the chamber is maintained at 250 mtorr with argon for five minutes. Each sample is then packaged in a sterilization pouch.

D. EtO Sterilization:

Samples are placed in a sterilization chamber which is then evacuated to about 2 psia. While maintaining this pressure the relative humidity in the chamber is raised to 60% and the temperature to 46° C. These conditions are maintained for one hour. The chamber is then charged with ethylene oxide, 12% in freon, to a final pressure of 22–23 psia. After two hours the chamber is evacuated to about 2 psia and then the system is brought up to atmosphere. The lens samples are then removed to the aeration chamber and aerated at elevated temperatures for a time sufficient to remove residual EtO levels of less than 25 ppm.

EXAMPLE 2

Protein Adsorption:

Human fibrinogen radiolabelled with $^{125}$Iodine was used to assess the protein repelling capability of the cross-linked coatings following EtO sterilization. Samples are incubated in Balanced Salt Solution (BSS) at 37° C. for one hour. This solution is then removed and replaced by a BSS solution containing 50 µg/mL $^{125}$I-fibrinogen. After incubating the samples at 37° C. for two hours they are removed, washed with BSS and their individual radioactivity levels determined.

The amount of adsorbed protein is reported in Table 1 as a fraction of that on uncoated control surfaces. The results show that PEO coatings which have been cross-linked by irradiation with high energy particles and/or radiation are very effective in reducing protein adsorption to PMMA even after EtO sterilization.

TABLE 1

NORMALIZED FIBRINOGEN ADSORPTION LEVELS ON UNCROSS-LINKED AND CROSS-LINKED PEO-COATED LENSES BEFORE AND AFTER ETHYLENE OXIDE STERILIZATION
ADSORBED FIBRINOGEN (NORMALIZED)

| IOL Material | UNCROSS-LINKED COATING | | CROSS-LINKED COATING | |
|---|---|---|---|---|
| | PRE-STERIL-IZATION | POST-STERIL-IZATION | PRE-STERIL-IZATION | POST-STERIL-IZATION |
| PMMA | $0.07 \pm 0.04$ (n = 12)† | $0.27 \pm 0.07$ (n = 12) | $0.08 \pm 0.01$ (n = 12) | $0.15 \pm 0.03$ (n = 12) |

†Values in parentheses are the number of samples, determined from the number of runs, each performed in triplicate. For example, n = 12 represents four runs, each performed in triplicate.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than the foregoing description.

I claim:

1. A PEO-coated implantable medical device which can be sterilized by ethylene oxide sterilization without substantial loss of the PEO coating's protein and/or cell repulsion ability, wherein the device comprises a PEO coating comprising cross-linked, α,ω-aldehyde-terminated PEO compounds having a number average molecular weight from 200–100,000, and wherein at least one of the α,ω-aldehydes of the PEO compounds is attached to the implantable medical device and the cross-linking is achieved by exposure to a high energy source.

2. The medical device of claim 1 wherein the α,ω-aldehyde-terminated PEO has a molecular weight from 1,500–10,000.

3. The medical device of claim 2 wherein the α,ω-aldehyde-terminated PEO has a molecular weight of about 8000.

4. The medical device of claim 1 wherein the high energy source is a source which results in the formation of one or more of the group consisting of free radicals, ions, electrons, protons, neutrons, alpha particles, beta particles, gamma radiation, X-ray radiation, and ultraviolet radiation.

5. The medical device of claim 4 wherein the high energy source is an argon plasma.

6. The medical device of claim 1 wherein the medical device is an intraocular lens.

\* \* \* \* \*